United States Patent
Andruzzi

(10) Patent No.: US 10,036,011 B2
(45) Date of Patent: Jul. 31, 2018

(54) SCAVENGER COMPOUNDS FOR IMPROVED SEQUENCING-BY-SYNTHESIS

(71) Applicant: QIAGEN Waltham, Inc., Waltham, MA (US)

(72) Inventor: Luisa Andruzzi, Concord, MA (US)

(73) Assignee: QIAGEN Waltham, INC., Waltham, MA (US)

( * ) Notice: Subject to any disclaimer, the term of this patent is extended or adjusted under 35 U.S.C. 154(b) by 0 days.

(21) Appl. No.: 15/427,832

(22) Filed: Feb. 8, 2017

(65) Prior Publication Data

US 2017/0233725 A1 Aug. 17, 2017

Related U.S. Application Data

(60) Provisional application No. 62/293,969, filed on Feb. 11, 2016.

(51) Int. Cl.
*C12N 15/64* (2006.01)
*C12N 15/10* (2006.01)

(52) U.S. Cl.
CPC ................ *C12N 15/1068* (2013.01)

(58) Field of Classification Search
None
See application file for complete search history.

(56) References Cited

U.S. PATENT DOCUMENTS

| | | | |
|---|---|---|---|
| 3,817,837 A | 6/1974 | Rubenstein et al. | 435/7.9 |
| 3,850,752 A | 11/1974 | Schuurs et al. | 435/7.93 |
| 3,939,350 A | 2/1976 | Kronick et al. | 250/365 |
| 3,996,345 A | 12/1976 | Ullman et al. | 436/537 |
| 4,275,149 A | 6/1981 | Litman et al. | 435/7.91 |
| 4,277,437 A | 7/1981 | Maggio | 422/401 |
| 4,366,241 A | 12/1982 | Tom et al. | 435/7.91 |
| 4,683,195 A | 7/1987 | Mullis et al. | 435/6.11 |
| 4,683,202 A | 7/1987 | Mullis | 435/91.2 |
| 6,664,079 B2 | 12/2003 | Ju et al. | 435/91.1 |
| 8,623,598 B2 | 1/2014 | Olejnik | 435/6.1 |
| 9,145,589 B2 | 9/2015 | Gordon et al. | 435/6.1 |
| 2010/0035253 A1* | 2/2010 | Gordon | C12Q 1/6825 435/6.11 |

OTHER PUBLICATIONS

Anderson, M. L. M. et al. (1985) "Quantitative Filter Hybridization," in *Nucleic Acid Hybridisation: A Practical Approach* (Hames, B. D., et al., Eds.), pp. 73-111, Oxford University Press, USA.
Chyan, Y.-J. et al. (1999) "Potent Neuroprotective Properties against the Alzheimer β-Amyloid by an Endogenous Melatonin-related Indole Structure, Indole-3-propionic Acid," *Journal of Biological Chemistry* 274(31), 21937-21942.
Dieffenbach, C. W. et al. (1995) *PCR Primer, A Laboratory Manual*, Cold Spring Harbor Laboratory Press, Plainview, N.Y.
Gülçin, I. (2006) "Antioxidant and antiradical activities of l-carnitine," *Life Sciences* 78(8), 803-811.
Martin, J. P. et al. (1987) "The role of oxygen radicals in dye-mediated photodynamic effects in *Escherichia coli* B," *Journal of Biological Chemistry* 262(15), 7213-7219.
Spagnoli, A. et al. (1991) "Long-term acetyl-L-carnitine treatment in Alzheimer's disease," *Neurology* 41(11), 1726-1732.

* cited by examiner

*Primary Examiner* — Suchira Pande
(74) *Attorney, Agent, or Firm* — Medlen & Carroll, LLP

(57) ABSTRACT

The present invention discloses methods of applications of indole-3-propionic acid, L-carnitine and O-acetyl-L-carnitine in one or more different reactive steps of a sequencing-by-synthesis workflow. The reactive steps employing these compounds include, but are not limited to, cleaving, imaging, incorporating bases and washing. The use of these new compounds provides improved sequencing performance including, but not limited to, lower error rates, higher sequence outputs and/or longer read lengths.

37 Claims, 10 Drawing Sheets

| Station | Step | Volume [ul] | Pump Speed [ul/s] | Pump Time [s] | Dwell Time [s] | Total Time Per Station [s] |
|---|---|---|---|---|---|---|
| 1 | Cleave | 100 | 67 | 1.5 | 120 | 121 |
| 2 | Dwell | 0 | 0 | 0.0 | 120 | 120 |
| 2 | Wash 11 | 990 | 27 | 36.7 | 0 | 37 |
| 3 | ExtA | 100 | 67 | 1.5 | 120 | 121 |
| 4 | ExtB | 100 | 67 | 1.5 | 150 | 151 |
| 5 | Wash | 330 | 27 | 12.2 | 0 | 12 |
| 5 | ImgAB* (100 each) | 200 | 27 | 7.4 | 0 | 7 |
| 11 | Imaging** | 0 | 0 | 0.0 | 560 | 560 |
| 20 | Wash | 330 | 27 | 12.2 | 0 | 12 |

**75 Tiles

SCAVENGER COMPOUNDS FOR IMPROVED SEQUENCING-BY-SYNTHESIS

FIELD OF THE INVENTION

The invention relates to methods, compositions, devices, systems and kits are described including, without limitation, reagents and mixtures for determining the identity of nucleic acids in nucleotide sequences using, for example, data obtained from sequencing by synthesis methods.

BACKGROUND

Over the past 25 years, the amount of DNA sequence information that has been generated and deposited into Genbank has grown exponentially. Traditional sequencing methods (e.g., for example Sanger sequencing) are being replaced by next-generation sequencing technologies that use a form of sequencing by synthesis (SBS), wherein specially designed nucleotides and DNA polymerases are used to read the sequence of chip-bound, single-stranded DNA templates in a controlled manner. To attain high throughput, many millions of such template spots are arrayed across a sequencing chip and their sequence is independently read out and recorded.

Systems for using arrays for DNA sequencing are known (e.g., Ju et al., U.S. Pat. No. 6,664,079). However, there is a continued need for methods and compositions for increasing the accuracy and/or efficiency of sequencing nucleic acid sequences and increasing the read lengths available for automated sequencing.

SUMMARY OF THE INVENTION

The invention relates to methods, compositions, devices, systems and kits as described including, without limitation, reagents and mixtures for determining the identity of nucleic acids in nucleotide sequences using, for example, data obtained from sequencing by synthesis methods. In one embodiment, the present invention contemplates applications of indole-3-propionic acid, L-carnitine and/or O-acetyl-L-carnitine, in one or more different reactive steps of a sequencing-by-synthesis workflow. The reactive steps employing these compounds can include, but are not limited to, the steps of cleaving, imaging, incorporating bases and washing. The use of these new compounds provides improved sequencing performance including, but not limited to, lower error rates, higher sequence outputs and/or longer read lengths.

In one embodiment, the present invention contemplates a method of incorporating labeled nucleotides, comprising: a) providing i) a plurality of nucleic acid primers and template molecules, ii) a polymerase, iii) a cleave reagent comprising a scavenger including, but not limited to indole-3-propionic acid and a carnitine-based compound, and iv) a plurality of nucleotide analogues wherein at least a portion of said nucleotide analogues is labeled with a label attached through a cleavable disulfide linker to the base; b) hybridizing at least a portion of said primers to at least a portion of said template molecules so as to create hybridized primers; c) incorporating a first labeled nucleotide analogue with said polymerase into at least a portion of said hybridized primers so as to create extended primers comprising an incorporated nucleotide analogue; and d) cleaving the cleavable linker of said incorporated nucleotide analogues with said cleave reagent. In one embodiment, said scavenger is indole-3-propionic acid. In one embodiment said scavenger is L-carnitine. In one embodiment, said scavenger is O-acetyl-L-carnitine. In one embodiment, said incorporated nucleotide analogues of step c) further comprise a removable chemical moiety capping the 3'-OH group. In one embodiment, the cleaving of step d) removes the removable chemical moiety capping the 3'-OH group. In a further embodiment, the method further comprises: d) incorporating a second nucleotide analogue with said polymerase into at least a portion of said extended primers. In one embodiment, said incorporating of a second nucleotide analogue is performed in the presence of a scavenger including, but not limited to, indole-3-propionic acid and a carnitine-based compound.

In yet another embodiment, the present invention contemplates a method of incorporating nucleotides, comprising: a) providing i) a plurality of nucleic acid primers and template molecules, and ii) an extend reagent, said extend reagent comprising polymerase, a plurality of nucleotide analogues, and a scavenger including, but not limited to, indole-3-propionic acid and a carnitine-based compound; b) hybridizing at least a portion of said primers to at least a portion of said template molecules so as to create hybridized primers; and c) exposing said hybridized primers to said extend reagent under conditions such that a first nucleotide analogue is incorporated into at least a portion of said hybridized primers so as to create extended primers comprising an incorporated nucleotide analogue. In one embodiment, said incorporated nucleotide analogue comprises a label attached through a cleavable disulfide linker to the base. In a preferred embodiment, said label is fluorescent. In one embodiment, said extend reagent further comprises cystamine. In a further embodiment, the method further comprises: d) cleaving the cleavable linker of said incorporated nucleotide analogue with a cleave reagent comprising a scavenger including, but not limited to, indole-3-propionic acid and a carnitine-based compound. In one embodiment, said scavenger is indole-3-propionic acid. In one embodiment said scavenger is L-carnitine. In one embodiment, said scavenger is O-acetyl-L-carnitine. In one embodiment, said incorporated nucleotide analogues prior to step d) further comprise a removable chemical moiety capping the 3'-OH group. In one embodiment, the cleaving of step d) removes the removable chemical moiety capping the 3'-OH group.

In yet another embodiment, the present invention contemplates a method of incorporating nucleotides, comprising: a) providing i) a plurality of nucleic acid primers and template molecules, ii) an extend reagent comprising polymerase and a plurality of nucleotide analogues, and iii) a wash reagent comprising a scavenger including, but not limited to, indole-3-propionic acid and a carnitine-based compound; b) hybridizing at least a portion of said primers to at least a portion of said template molecules so as to create hybridized primers; c) exposing said hybridized primers to said extend reagent under conditions such that a first nucleotide analogue is incorporated into at least a portion of said hybridized primers so as to create extended primers comprising an incorporated nucleotide analogue; d) washing said extended primers with said wash reagent. In one embodiment, said incorporated nucleotide analogue comprises a label attached through a cleavable disulfide linker to the base. In a preferred embodiment, said label is fluorescent. In one embodiment, said extend reagent further comprises cystamine. In a further embodiment, the method further comprises e) detecting said label of a first labeled nucleotide analogue. In one embodiment, said detecting of step e) is performed in the presence of a scavenger including, but not limited to, indole-3-propionic acid and a carnitine-based compound. In one embodiment, said scavenger is indole-3- propionic acid. In one embodiment said scavenger is L-carnitine. In one embodiment, said scavenger is O-acetyl-L-carnitine.

In yet another embodiment, the present invention contemplates a method of incorporating labeled nucleotides, comprising: a) providing i) a plurality of nucleic acid primers and template molecules, ii) an extend reagent comprising polymerase and a plurality of nucleotide analogues wherein at least a portion of said nucleotide analogues is labeled, and iii) an image reagent comprising a scavenger including, but not limited to, indole-3-propionic acid and a carnitine-based compound; b) hybridizing at least a portion of said primers to at least a portion of said template molecules so as to create hybridized primers; c) exposing said hybridized primers to said extend reagent under conditions such that a first labeled nucleotide analogue is incorporated into at least a portion of said hybridized primers so as to create extended primers comprising an incorporated nucleotide analogue; and d) detecting said label of said first labeled nucleotide analogue with said image reagent. In one embodiment, said label is attached through a cleavable disulfide linker to the base. In a preferred embodiment, said label is fluorescent. In one embodiment, said extend reagent further comprises cystamine. In a further embodiment, the method further comprises e) cleaving the cleavable linker of said incorporated nucleotide analogue with a cleave reagent comprising a scavenger including, but not limited to, indole-3-propionic acid and a carnitine-based compound. In one embodiment, said scavenger is indole-3-propionic acid. In one embodiment said scavenger is L-carnitine. In one embodiment, said scavenger is O-acetyl-L-carnitine. In one embodiment, said incorporated labeled nucleotide analogue of step d) further comprises a removable chemical moiety capping the 3'-OH group. In one embodiment, the cleaving of step e) removes the removable chemical moiety capping the 3'-OH group.

The present invention also contemplates compositions and mixtures. In one embodiment, the present invention contemplates a cleave reagent comprising i) a reducing agent, and ii) a scavenger including, but not limited to, indole-3-propionic acid and a carnitine-based compound. In one embodiment reducing agent is Tris(2-carboxyethyl) phosphine) ("TCEP"). In yet another embodiment, the present invention contemplates an extend reagent comprising polymerase, a plurality of nucleotide analogues, and a scavenger including, but not limited to, indole-3-propionic acid and a carnitine-based compound. In yet another embodiment, the present invention contemplates a wash reagent comprising a scavenger including, but not limited to, indole-3-propionic acid and a carnitine-based compound, said scavenger in a buffer. In one embodiment, said buffer is a Tris buffer. In still another embodiment, the present invention contemplates an image reagent comprising a scavenger including, but not limited to, indole-3-propionic acid and a carnitine-based compound, said scavenger in a buffer. In one embodiment, said buffer is a Hepes buffer.

The present invention also contemplates kits and disposables for automated sequencing systems and devices. In one embodiment, the present invention contemplates a kit, comprising (preferably in separate containers) a cleave reagent and an extend reagent, wherein the cleave reagent comprises i) a reducing agent, and ii) a scavenger including, but not limited to, indole-3-propionic acid and a carnitine-based compound, and wherein the extend reagent comprises polymerase, a plurality of nucleotide analogues, and a scavenger including, but not limited to, indole-3-propionic acid and a carnitine-based compound. In one embodiment, the kit further comprises a wash reagent and/or an imaging reagent.

The present invention also contemplates systems and devices. In one embodiment, the present invention contemplates a system comprising primers hybridized to template in solution, said solution comprising immobilized a scavenger including, but not limited to, indole-3-propionic acid and a carnitine-based compound. In one embodiment, said hybridized primers and template are immobilized (e.g., on a solid support, in a channel, on beads, etc.). In one embodiment, said hybridized primers and template are in a flow cell (e.g. a flow cell in fluidic communication with a reagent reservoir). In one embodiment, at least a portion of the flow cell is transparent (allowing for imaging). Such flow cells are described in U.S. Pat. No. 8,940,481, hereby incorporated by reference. In one embodiment, the present invention contemplates a system wherein the flow cells are moved to different stations. Such a systems is described in U.S. Pat. No. 9,145,589, hereby incorporated by reference.

DEFINITIONS

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but also plural entities and also includes the general class of which a specific example may be used for illustration. The terminology herein is used to describe specific embodiments of the invention, but their usage does not delimit the invention, except as outlined in the claims.

The term "about" as used herein, in the context of any of any assay measurements refers to +/−5% of a given measurement.

The term "scavenger" as used herein, refers to any molecule and/or compound that reacts with, and neutralizes, toxic molecules that have the capability of causing DNA photodamage and/or scission. For example, a scavenger may include, but is not limited to, an oxygen radical scavenger.

The term "linker" as used herein, refers to any molecule capable of attaching a label and/or chemical moiety that is susceptible to omolytic cleavage that may produce toxic radical products. For example, a linker may include, but is not limited to, a disulfide linker and/or an azide linker.

The term "attached" as used herein, refers to any interaction between a first molecule (e.g., for example, a nucleic acid) and a second molecule (e.g., for example, a label molecule). Attachment may be reversible or irreversible. Such attachment includes, but is not limited to, covalent bonding, ionic bonding, Van der Waals forces or friction, and the like.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand. Such nucleic acids may include, but are not limited to, cDNA, mRNA or other nucleic acid sequences.

The term "an isolated nucleic acid", as used herein, refers to any nucleic acid molecule that has been removed from its natural state (e.g., removed from a cell and is, in a preferred embodiment, free of other genomic nucleic acid).

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

Low stringency conditions comprise conditions equivalent to binding or hybridization at 42° C. in a solution consisting of 5×SSPE (43.8 g/l NaCl, 6.9 g/l NaH2PO4.H2O and 1.85 g/l EDTA, pH adjusted to 7.4 with NaOH), 0.1% SDS, 5×Denhardt's reagent {50×Denhardt's contains per 500 ml: 5 g Ficoll (Type 400, Pharmacia), 5 g BSA (Fraction V; Sigma)} and 100 µg/ml denatured salmon sperm DNA followed by washing in a solution comprising 5×SSPE, 0.1% SDS at 42° C. when a probe of about 500 nucleotides in length. is employed. Numerous equivalent conditions may also be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) may also be used.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the Tm of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an anti-parallel configuration. A hybridization complex may be formed in solution (e.g., C0 t or R0 t analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "Tm" is used in reference to the "melting temperature." The melting temperature is the temperature at which a population of double-stranded nucleic acid molecules becomes half dissociated into single strands. As indicated by standard references, a simple estimate of the Tm value may be calculated by the equation: $Tm=81.5+0.41$ (% G+C), when a nucleic acid is in aqueous solution at 1M NaCl. Anderson et al., "Quantitative Filter Hybridization" In: Nucleic Acid Hybridization (1985). More sophisticated computations take structural, as well as sequence characteristics, into account for the calculation of Tm.

As used herein the term "stringency" is used in reference to the conditions of temperature, ionic strength, and the presence of other compounds such as organic solvents, under which nucleic acid hybridizations are conducted. "Stringency" typically occurs in a range from about Tm to about 20° C. to 25° C. below Tm. A "stringent hybridization" can be used to identify or detect identical polynucleotide sequences or to identify or detect similar or related polynucleotide sequences. For example, when fragments are employed in hybridization reactions under stringent conditions the hybridization of fragments which contain unique sequences (i.e., regions which are either non-homologous to or which contain less than about 50% homology or complementarity) are favored. Alternatively, when conditions of "weak" or "low" stringency are used hybridization may occur with nucleic acids that are derived from organisms that are genetically diverse (i.e., for example, the frequency of complementary sequences is usually low between such organisms).

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of a target sequence of interest. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Amplification" is defined as the production of additional copies of a nucleic acid sequence and is generally carried out using polymerase chain reaction. Dieffenbach C. W. and G. S. Dveksler (1995) In: PCR Primer, a Laboratory Manual, Cold Spring Harbor Press, Plainview, N.Y.

As used herein, the term "polymerase chain reaction" ("PCR") refers to the method of K. B. Mullis U.S. Pat. Nos. 4,683,195 and 4,683,202, herein incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxy-ribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers; to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "label" or "detectable label" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabeads®), fluorescent dyes (e.g., fluorescein, texas red, rhodamine, green fluorescent protein, and the like), radiolabels (e.g., 3H, 125I, 35S, 14C, or 32P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277,437; 4,275,149; and 4,366,241 (all herein incorporated by reference).

In a preferred embodiment, the label is typically fluorescent and is linked to the base of the nucleotide. For cytosine and thymine, the attachment is usually to the 5-position. For the other bases, a deaza derivative is created and the label is linked to a 7-position of deaza-adenine or deaza-guanine.

The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

The term "luminescence" and/or "fluorescence", as used herein, refers to any process of emitting electromagnetic radiation (light) from an object, chemical and/or compound. Luminescence and/or fluorescence results from a system which is "relaxing" from an excited state to a lower state with a corresponding release of energy in the form of a photon. These states can be electronic, vibronic, rotational, or any combination of the three. The transition responsible for luminescence can be stimulated through the release of energy stored in the system chemically or added to the system from an external source. The external source of energy can be of a variety of types including, but not limited to, chemical, thermal, electrical, magnetic, electromagnetic, physical or any other type capable of causing a system to be excited into a state higher than the ground state. For example, a system can be excited by absorbing a photon of light, by being placed in an electrical field, or through a chemical oxidation-reduction reaction. The energy of the photons emitted during luminescence can be in a range from low-energy microwave radiation to high-energy x-ray radiation. Typically, luminescence refers to photons in the range from UV to IR radiation.

BRIEF DESCRIPTION OF THE FIGURES

FIG. 1A: The IPA runs evaluated fifteen (15) flow cells and the gallic acid runs evaluated seven (7) flow cells. FIG. 1B: Average bead loading for all flow cells was about 430,000 beads/tile.

FIG. 9 describes one embodiment of the present invention, comprising a table of an SBS method doing different steps at different stations. By way of example, each station and conditions are is associated with a particular step: Including step 1) Cleave; step 2) Dwell; step 3) Wash 11; step 4) ExtA; step 5) ExtB; step 6) Wash; step 7) ImgAB*; step 8) Imaging**; and step 9) Wash. All conditions are further described in the specification.

DETAILED DESCRIPTION OF THE INVENTION

Figure 1A:
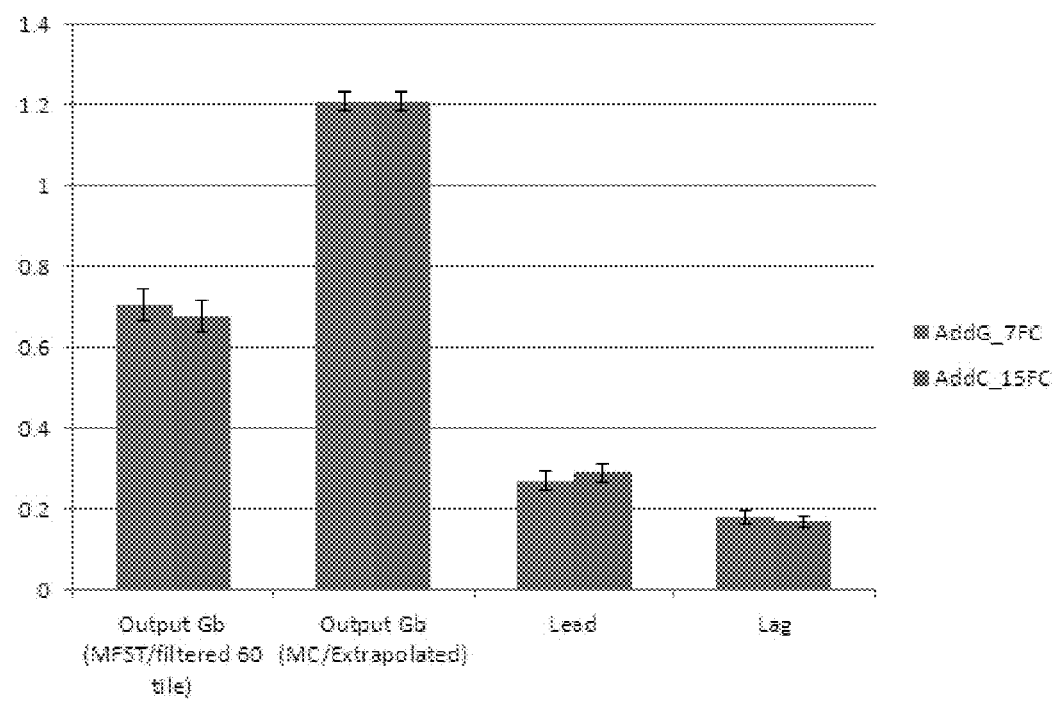
FIG. 1A-1B presents exemplary data comparing indole-3-propionic acid (IPA) and gallic acid (GA).

The invention relates to methods, compositions, devices, systems and kits as described including, without limitation, reagents and mixtures for determining the identity of nucleic acids in nucleotide sequences using, for example, data obtained from sequencing by synthesis methods.

In one embodiment, the present invention contemplates a method comprising indole-3-propionic acid (IPA), a potent radical scavenger and a singlet oxygen quencher, as an additive to a cleave reagent utilized in sequencing by synthesis (SBS). Although it is not necessary to understand the mechanism of an invention, it is believed that the presently disclosed method provides a significant improvement in the efficacy of a cleave reaction thus allowing diminished sequencing error rate and enhancement of filtered sequence read output. It is further believed that IPA can also be used during the steps of imaging, base incorporation (e.g., extension) and washing to achieve longer sequencing reads.

In one embodiment, the present invention also contemplates the use of additional compounds for use as either cocktail components with IPA or standalone additives to further improve cleave chemistry and sequencing performance. These additional compounds include, but are not limited to, L-carnitine and/or O-acetyl-L-carnitine. In one embodiment, the present invention also contemplates the use of radical scavenger including, but not limited to, indole-3-propionic acid, L-carnitine and/or O-acetyl-L-carnitine.

I. Sequencing-By Synthesis (SBS)

The invention relates to methods and compositions for determining the identity of nucleic acids in nucleotide sequences using, for example, data obtained from sequencing by synthesis methods. In sequencing by synthesis, nucleotides conjugated with fluorescent markers that incorporate into a growing double-stranded nucleic acid from the single strand are detected. For example, one may immobilize template DNA on a solid surface by its 5' end. One may accomplish this by annealing a sequencing primer to a consensus sequence and introducing DNA polymerase and fluorescent nucleotide conjugates (alternatively, a self-priming hairpin can be introduced by PCR or ligation to the template). One detects nucleotide incorporation using a laser microarray scanner or fluorescent microscope by correlating a particular fluorescent marker to a specific nucleotide. After each nucleotide is incorporated and the fluorescent signal is detected, one bleaches or removes the fluorescent moiety from the nucleotide conjugate so as to prevent the accumulation of a background signal.

In one embodiment, the present invention contemplates DNA sequencing by synthesis using an automated instrument, as well as methods and compositions useful for sequencing using such an instrument. In one embodiment, the instrument comprises a flow cell with at least two fluidics ports, a substrate with sequenceable nucleic acid molecules attached to the substrate, reagent and waste reservoirs and fluidic system connecting the reservoirs to the flow cell. The flow cell is interfaced with a detection system to monitor the incorporation of the nucleotides.

In one embodiment, the sequencing by synthesis is carried out using reversibly terminating nucleotides and polymerase. The nucleotides comprise a protective group at their 3'-OH which prevents multiple incorporations and allows for accurate decoding of the sequence. Once incorporated, the protective groups can be cleaved with high efficiency and specificity to allow subsequent nucleotide incorporations. The nucleotides may also comprise a detectable label which can be cleaved after the detection.

In one embodiment, the present invention contemplates a SBS method comprising the steps shown in Table 1. Olejink et al., "Methods And Compositions For Inhibiting Undesired Cleaving Of Labels" U.S. Pat. No. 8,623,598 (herein incorporated by reference in its entirety).

TABLE 1

An Exemplary SBS Workflow

| | | Fluid Movements | | | | |
|---|---|---|---|---|---|---|
| Step | Reagent | Volume mL | Speed mL/s | Station Number | Temp ° C. | Time [s] |
| 1. Dispense Reagent | Reagent 1 | 100 | 67 | 3 | 65 | 7 |
| 2. Incubate Reagent | Reagent 1 | n/a | n/a | 3 | 65 | 210 |
| 3. Dispense Reagent | Reagent 2 | 100 | 67 | 4 | 65 | 7 |
| 4. Incubate Reagent | Reagent 2 | n/a | n/a | 4 | 65 | 210 |
| 5. Dispense Reagent | Reagent 3 | 330 | 27 | 5 | Ambient | 12 |
| 6. Dispense Reagent | Reagent 4 + 5 | 200 | 27 | 5 | Ambient | 15 |
| 7. Image | n/a | n/a | n/a | 11 | Ambient | 210 |
| 8. Dispense Reagent | Reagent 3 | 330 | 27 | 20 | 65 | 12 |
| 9. Dispense Reagent | Reagent 6 | 100 | 67 | 1 | 65 | 7 |
| 10. Incubate Reagent | Reagent 6 | n/a | n/a | 1 | 65 | 210 |
| 11. Incubate Reagent | Reagent 6 | n/a | n/a | 2 | 65 | 210 |

TABLE 1-continued

An Exemplary SBS Workflow

| | | Fluid Movements | | | | |
|---|---|---|---|---|---|---|
| Step | Reagent | Volume mL | Speed mL/s | Station Number | Temp ° C. | Time [s] |
| 12. Dispense Reagent | Reagent 7 | 990 | 27 | 2 | 65 | 37 |
| 13. Go to Step 1 | | | | | | |

Reagent 1 = Extend A; Reagent 2 = Extend B; Reagent 3 = Wash; Reagent 4 = Image A; Reagent 5 = Image B; Reagent 6 = Cleave; and Reagent 7 = Wash 11

Washing solution compositions may include, but are not limited to:

| | Component | Conc |
|---|---|---|
| Wash (9, 10) | Tween | 0.05% |
| | TrisHCl (pH 8.8) (mM) | 50 |
| | NaCl (mM) | 50 |
| | EDTA (mM) | 1 |
| | Methylenediphosphonic acid (PcPi) (mM) | 1 |
| Wash (11) | Tween | 0.05% |
| | TrisHCl (pH 8.8) (mM) | 50 |
| | NaCl (mM) | 50 |
| | EDTA (mM) | 1 |
| | Cystamine (mM) | 10 |
| Wash (12) | Tween | 0.05% |
| | TrisHCl (pH 8.8) (mM) | 50 |
| | NaCl (mM) | 50 |
| | EDTA (mM) | 1 |

In one embodiment, the SBS method comprises doing different steps at different stations. By way of example, each station is associated with a particular step:

A. SBS Cleavage Step

A reactive step in a method for sequencing by synthesis using cleavable fluorescent nucleotide reversible terminators comprises cleaving a fluorescent label from a nucleotide analogue molecule. In one embodiment, the fluorescent label may be covalently attached via a linker molecule to the heterocyclic base of an incorporated nucleotide analogue molecule (See U.S. Pat. No. 6,664,079, hereby incorporated by reference). Conceivably, the efficacy of the cleaving step may be reflected not only in the efficiency of the fluorescent label cleavage but also in the mitigation of by-product formation due to radical pathways involved in the omolytic scission of the linker molecule to release the fluorescent label. Although it is not necessary to understand the mechanism of an invention, it is believed that an effective cleave step plays a role in single nucleotide incorporation throughout the sequencing reaction which may control the accuracy of high throughput sequencing.

Gallic acid (GA) has been shown to improve sequencing performance and allow the system to provide a filtered trimmed sequence output of 1 Gb. Gallic acid is used herein for performance benchmarking of indole-3-propionic acid.

B. Extension Step

In one embodiment, the present invention contemplates a series of method steps performed by an automated sequencing by synthesis instrument. See U.S. Pat. No. 9,145,589, hereby incorporated by reference. In one embodiment, the instrument is comprised of numerous reagent reservoirs (see, Table 1). Each reagent reservoir has a specific reactivity reagent dispensed within the reservoir to support the SBS process, for example:

1) Extend A Reagent: Comprises reversibly terminated labeled nucleotides and polymerase. The composition of Extend A is as follows:

| Component | Conc |
|---|---|
| PNSE (% wt/vol) | 0.005% |
| Tris x HCl (pH 8.8), mM | 50 |
| NaCl (mM) | 50 |
| EDTA (mM) | 1 |
| MgSO4 (mM) | 10 |
| Cystamine (mM) | 1 |
| Glycerol (% wt/vol) | 0.01% |
| Therminator IX* (U/ml) | 10 |
| N3-dCTP (μM) | 3.83 |
| N3-dTTP (μM) | 3.61 |
| N3-dATP (μM) | 4.03 |
| N3-dGTP (μM) | 0.4 |
| Alexa488-dCTP (nM) | 550 |
| R6G-dUTP (nM) | 35 |
| ROX-dATP (nM) | 221 |
| Cy5-dGTP (nM) | 66 |

*with Alkylated free Cysteine

2) Extend B Reagent: Comprises reversibly terminated unlabeled nucleotides and polymerase, but lacks labeled nucleotide analogues. The composition of Extend B is as follows:

| Component | Conc |
|---|---|
| PNSE (% wt/vol) | 0.005% |
| Tris x HCl (pH 8.8), mM | 50 |
| NaCl (mM) | 50 |
| EDTA (mM) | 1 |
| MgSO4 (mM) | 10 |
| Glycerol (% wt/vol) | 0.01% |
| Therminator IX* (U/ml) | 10 |
| N3-dCTP (μM) | 21 |
| N3-dTTP (μM) | 17 |
| N3-dATP (μM) | 21 |
| N3-dGTP (μM) | 2 |

*Alkylated free Cysteine

3) Wash solution 1
  a detergent (e.g., polysorbate 20)
  citrate buffer (e.g., saline)
4) Cleave Reagent: A cleaving solution composition is as follows:

| Component | Conc |
|---|---|
| NaOH (mM) | 237.5 |
| TrisHCl (pH 8.0) (mM) | 237.5 |
| TCEP (mM) | 50 |

5) Wash solution 2
  a detergent (e.g., polysorbate 20)
  a tris(hydroxymethyl)aminomethane (Tris) buffer.

Of course, the present invention is not limited to any particular concentrations of reagents in these solutions and other buffers and detergents can be employed. Nonetheless, in order to achieve high throughput rates, the incorporation reactions and the cleavage reactions are desired to be fast. In one embodiment, high reaction rates are achieved by increasing the concentration of reagents, agitation, pH or temperature (or the combination of all these factors). The incorporation rate in addition is dependent on the specific activity and processivity of the polymerase used. In one particular embodiment (which is provided by way of a non-limiting example), the reagent solutions may have the following compositions and concentration ranges:

1) Extend A Reagent—reversibly terminated labeled (1 nM to 1 µM) and non-labeled nucleotides (1 µM to 100 µM) and a first polymerase (1-500 µg/ml));
2) Extend B Reagent—reversibly terminated non-labeled nucleotides (1 µM to 100 µM) and a second polymerase (1-500 µg/ml));
3) Wash 1 Reagent: (3×SSC, 0.02% Tween 20);
4) Cleave Reagent: (50-100 mM TCEP);
5) Wash 2 Reagent: (100 mM Tris-HCl, 0.02% Tween 20, 10 mM KCl, 20 mM $(NH_2)_2SO_4$.

In one embodiment, a first polymerase incorporates labeled nucleotides better than a second polymerase, which incorporates unlabeled nucleotides more efficiently. Examples of commercially available polymerases that can be used include, but are not limited to, Therminator I-III. These polymerases are derived from *Thermococcus* sp. and carry mutations allowing for incorporation of modified nucleotides.

In one embodiment, a sequenceable DNA molecule (i.e., for example, a DNA molecule that is preferably loaded on the chip or slide) is subjected to SBS reagents and compositions compatible with an SBS instrument, and the sequencing is performed using an automated protocol (see, Table 1). Again, it is not intended that the present invention be limited to any precise protocol or series of method steps. The order and number of steps can vary, as well as the time taken for each step. By way of a non-limiting example, in one embodiment, the instrument protocol comprises (and is configured) as follows:

1. Extend A Reagent: 0.5-5 minutes (delivery+agitation)
2. Extend B Reagent: 1-20 minutes (delivery+agitation)
3. Wash 2 Reagent: 5-10 minutes (10-20× delivery and agitation followed by flow cell evacuation)
4. Image Reagent. The imaging reagent solution (either solution A or B) is as follows:

|  | Component | Conc |
|---|---|---|
| Image A | Hepes-Na, pH 7.5, mM | 100 |
|  | NaI (mM) | 1 |
|  | Glucose oxidase (U/ml) | 5 |
|  | EGTA (µM) | 25 |
|  | Glycerol (% wt/vol) | 0.25 |
| Image B | Hepes-Na, pH 7.5, mM | 100 |
|  | NaCl (mM) | 300 |
|  | Glucose (mM) | 100 |
|  | Trolox (mM) | 2.4 |

5. Cleave Reagent (e.g., Cleave A and B): 1-5 minutes (delivery+agitation)
6. Wash 1 Reagent: 5-10 minutes (10-20× delivery and agitation followed by flow cell evacuation)
7. Wash 2 Reagent: 5-10 minutes (10-20× delivery and agitation followed by flow cell evacuation)
8. Go to step 1

This series of steps may be repeated as a cycle as many times as desired and images may be taken and subsequently analyzed to decode the DNA sequence of the template DNA molecule present at each location. As noted above, in one embodiment, one or more of these steps is associated with an instrument "station" wherein each station has the requisite reagent and/or dispensing elements to perform the step. Flow cells are moved from one station to another station in order to carry out each step of the sequencing protocol. Any one of these steps can be done at two stations if desired, i.e. a step taking a longer time can be completed over the course of two stations, each station doing a part (e.g. half of the step).

In one embodiment, a cycle may comprise incubating with eight nucleotide analogues including, but not limited to, four nucleotide analogues (e.g., A, T, C, G) that are cleavably labeled and reversibly terminated and/or four nucleotide analogues (e.g., A, T, G, C) that are unlabeled and reversibly terminated.

In one embodiment, the concentration of the labeled nucleotide analogues are at a relatively low concentration. Although it is not necessary to understand the mechanism of an invention, it is believed that the labeled nucleotide analogue concentration is just low enough to be incorporated into a substantial portion of the plurality of primers such that the label is visible and can be detected. Detection may be observed whether the primers are detached or self-priming hairpins hybridized to a template DNA.

In one embodiment, the concentration of the unlabeled analogues are at a relatively high concentration. Although it is not necessary to understand the mechanism of an invention, it is believed that the unlabeled analogue high concentration is capable of driving extensions to completion, and avoid the use of primers, whether they be detached primers or self-priming hairpins, that lack incorporation of a first nucleotide analogue. It has been found empirically that the use of unlabeled nucleotides improves read lengths, and reduces lead and lag.

III. Reactive Oxygen Species Scavengers

In one embodiment, the present invention contemplates an SBS method comprising a radical oxygen species scavenger compound including, but not limited to, indole-3-propionic acid, L-carnitine and/or O-acetyl-L-carnitine. Any one of these compounds, or any combination of these compounds, are contemplated as radical scavengers in any SBS reactive step, as well as in multiple steps. See, for example, Table 1 and the series of steps (provided by way of example). In some embodiments, one or more of these compounds may be included in the cleaving step, an imaging step, a base incorporation step (extension) and/or a wash step (in each step or combination of steps, or even in all of these steps). Although it is not necessary to understand the mechanism of an invention, it is believed that oxygen radical species may form due to an interaction between organic dyes and radiation during SBS and may be responsible for DNA photodamage and read length scission. It is further believed that quenching of radical oxygen species can lead to longer read length and a more efficient SBS method. For example, radical oxygen species that form during a cleaving step may carry over into subsequent SBS steps of the workflow that can be responsible for less efficient base incorporation. Therefore, the presence of a scavenger (e.g. radical oxygen scavenger) in the cleaving step (e.g., Cleave Reagent additive), base incorporation step (e.g., Extend A or Extend B Reagent additive), imaging step (e.g., Image Reagent additive) and wash steps (e.g., Wash Reagent additive) can lead to improved overall efficiency of the sequencing-by-synthesis reaction thereby resulting in longer read lengths.

A. Indole-3-propionic Acid (IPA)

Indole-3-propionic acid (IPA), a close relative molecule of melatonin, is an endogenous substance and may be found in the plasma and cerebrospinal fluid of humans. It is believed to be a potent radical scavenger and singlet oxygen quencher. Below a model mechanism of action for scavenging free radical is outlined. Upon initial reaction with a hydroxyl radical IPA is oxidized to a kynuric acid. Such mechanism can be extended to free radicals other than hydroxyl.

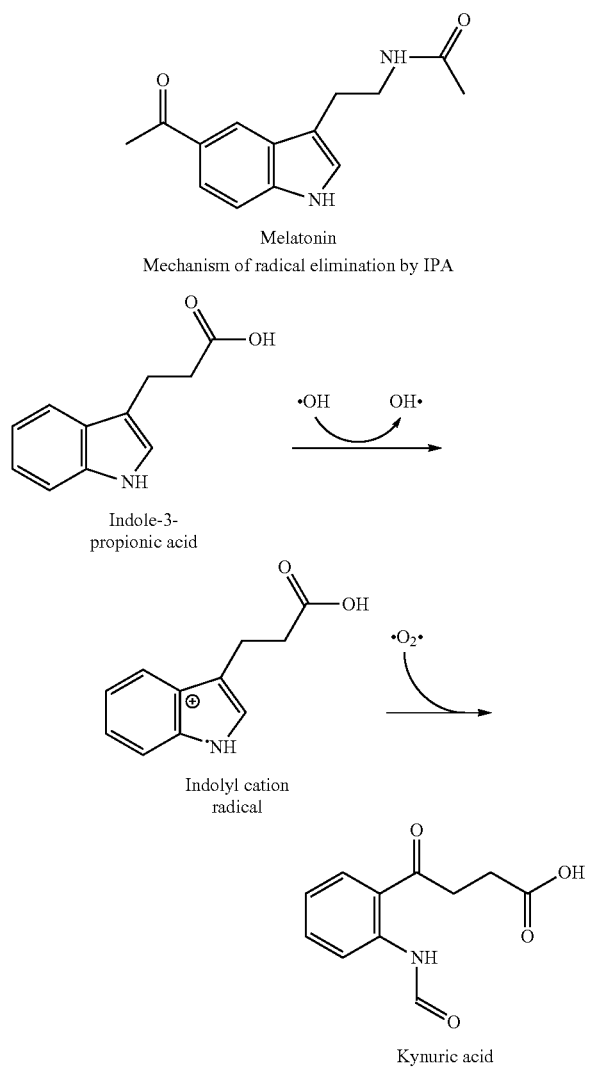

Melatonin
Mechanism of radical elimination by IPA

Indole-3-propionic acid

Indolyl cation radical

Kynuric acid

IPA has been demonstrated to prevent formation of beta-amyloid fibrils, leading to neuroprotective properties against Alzheimer disease. J. Biol. Chem. 274:21937 (1999); and J. Biol. Chem. 262:7213 (1987). As IPA is believed devoid of polyphenolic OH groups that are present in the reference reagent gallic acid, these groups are thought to be responsible for gallic acid's $SiO_2$ attack. Consequently, no reactivity of IPA with $SiO_2$ is anticipated based on its chemical architecture.

Due to its efficacy at quenching radical pathways, coupled with its mild chemical nature, IPA was evaluated for enhancement of Cleave Reagent performance in the sequencing workflow. The cleaving reactive step involves omolytic cleavage of a di-sulfide bond in the linker arm off of the heterocyclic base with concomitant release of a fluorescent label from the incorporating nucleotide. Although it is not necessary to understand the mechanism of an invention, it is believed that during this cleaving reaction radical oxygen species may form and their build up within the flow cell may impair efficiency of the next base incorporation cycle.

In one embodiment, the present invention contemplates a cleaving reactive step comprising an effective radical scavenger that shuts down radical pathways and prevents formation of radical species. In one embodiment, the reduced concentration of oxidative radicals improves the efficiency of the subsequent nucleotide base extension steps. Although it is not necessary to understand the mechanism of an invention, it is believed that this improved base incorporation efficiency beneficially impacts lead values, error rates, filtered sequence outputs and false positive rates.

Figure 2:
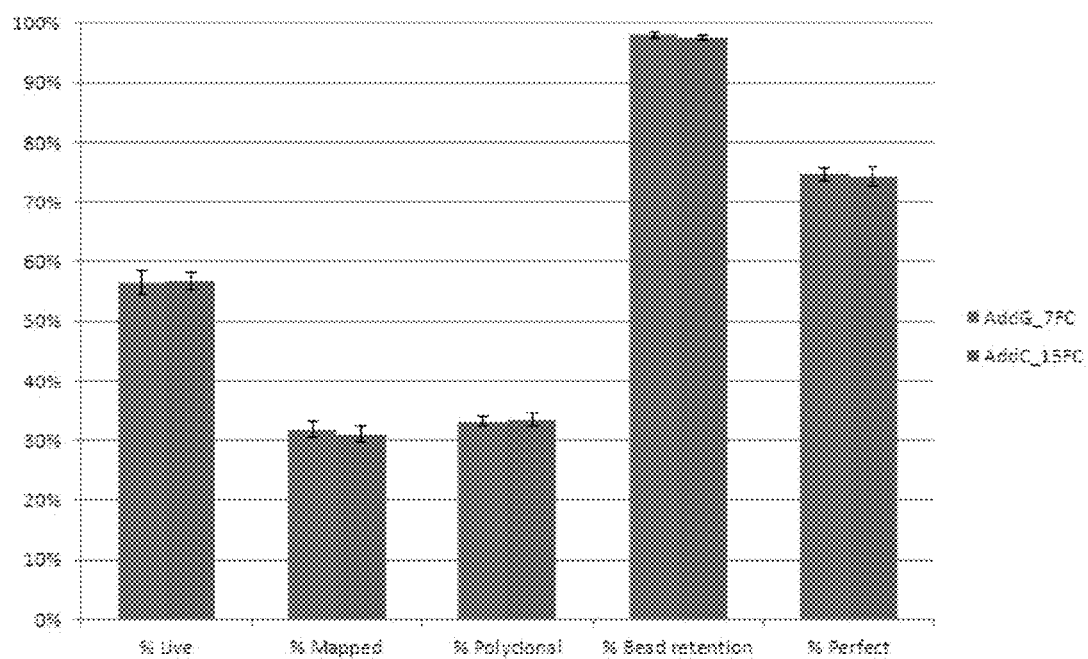
FIG. 2 presents exemplary KPI data based upon the IPA vs. gallic acid comparisons according to Example III.
Figure 3A:
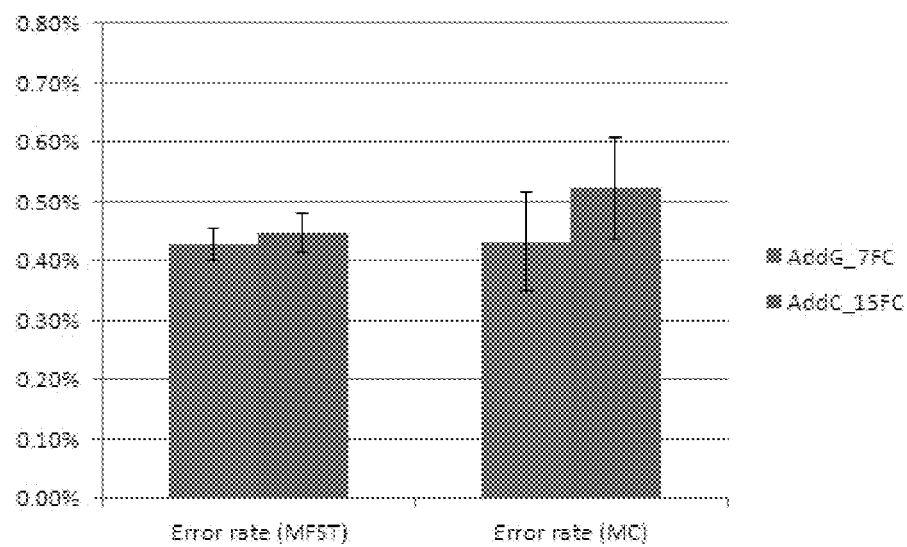
FIGS. 3A and 3B present exemplary KPI data based upon the IPA vs. gallic acid comparisons according to Example III.
Figure 3B:
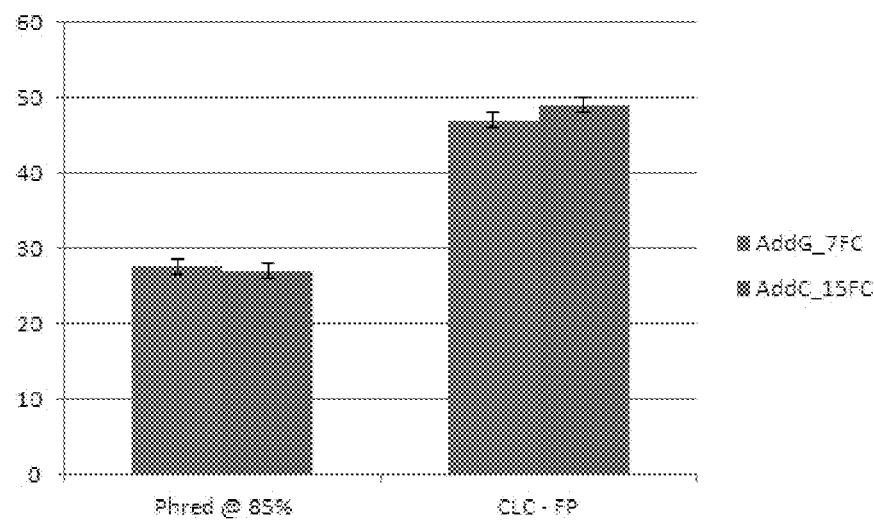

IPA testing was performed using four different reading instruments and a gene panel pool across all sequencing runs. See, Example III. IPA and the reference cleave reagent (e.g., gallic acid) were used to sequence clonally amplified gene panel beads (e.g., for example, an NA12878 barcoded library and/or a 101× gene panel) on each instrument. Finally, sequencing metrics were analyzed to provide both system and application KPI's, i. e., error rate/output (Gb) and false positive rate. See, FIG. 2, and FIGS. 3A & 3B. IPA was found to be comparable to the reference cleave reagent, gallic acid, for sequencing performance and superior in terms of reliability, specifically for preventing delamination of flow cell and bead loss during sequencing. Much improved compatibility with instrument hardware was also observed when IPA was used, for example, an inspection of sequencing waste found the solution to be clear, transparent and free of precipitate after a sequencing run.

IPA was initially tested for solubility and stability in Cleave Reagent formulations. It was found to be highly soluble over a range of concentrations and stable against discoloration and precipitation even upon prolonged storage at room temperature. IPA was then tested by sequencing in a head-to-head comparison with the reference cleaving reagent, gallic acid, to provide a performance benchmark. IPA was implemented into a sequencing workflow as a standalone powder component to the cleave reagent. See, Example IV.

Figure 1B:
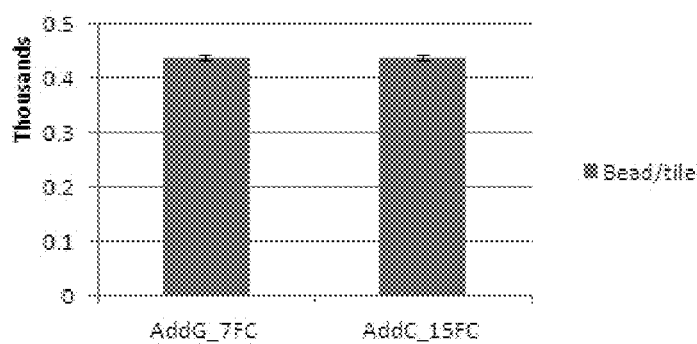
Figure 4:
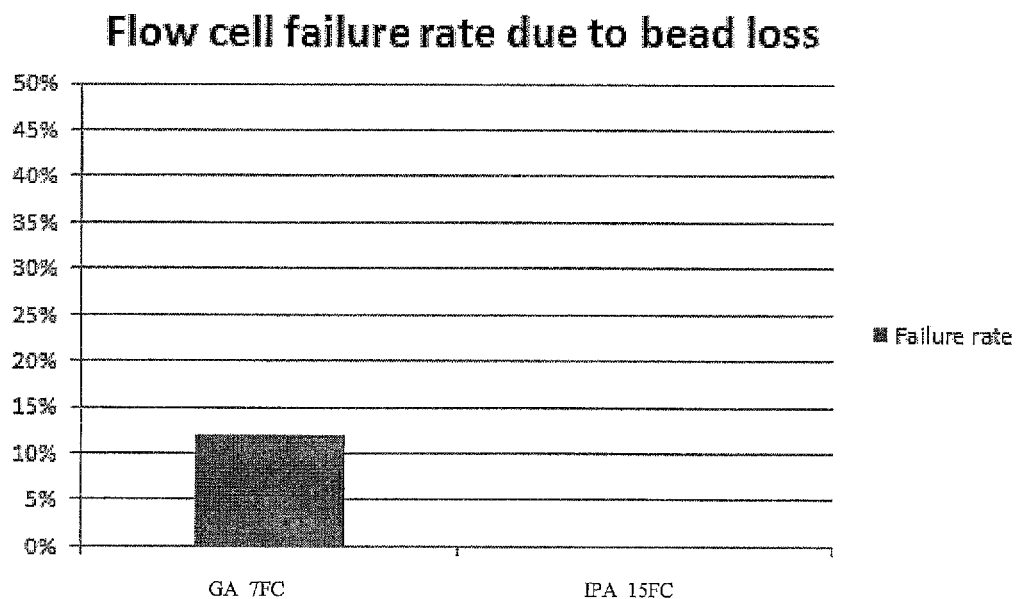
FIG. 4 presents exemplary data showing the relative bead loss in flow cells during runs comparing IPA and gallic acid.
Figure 8:
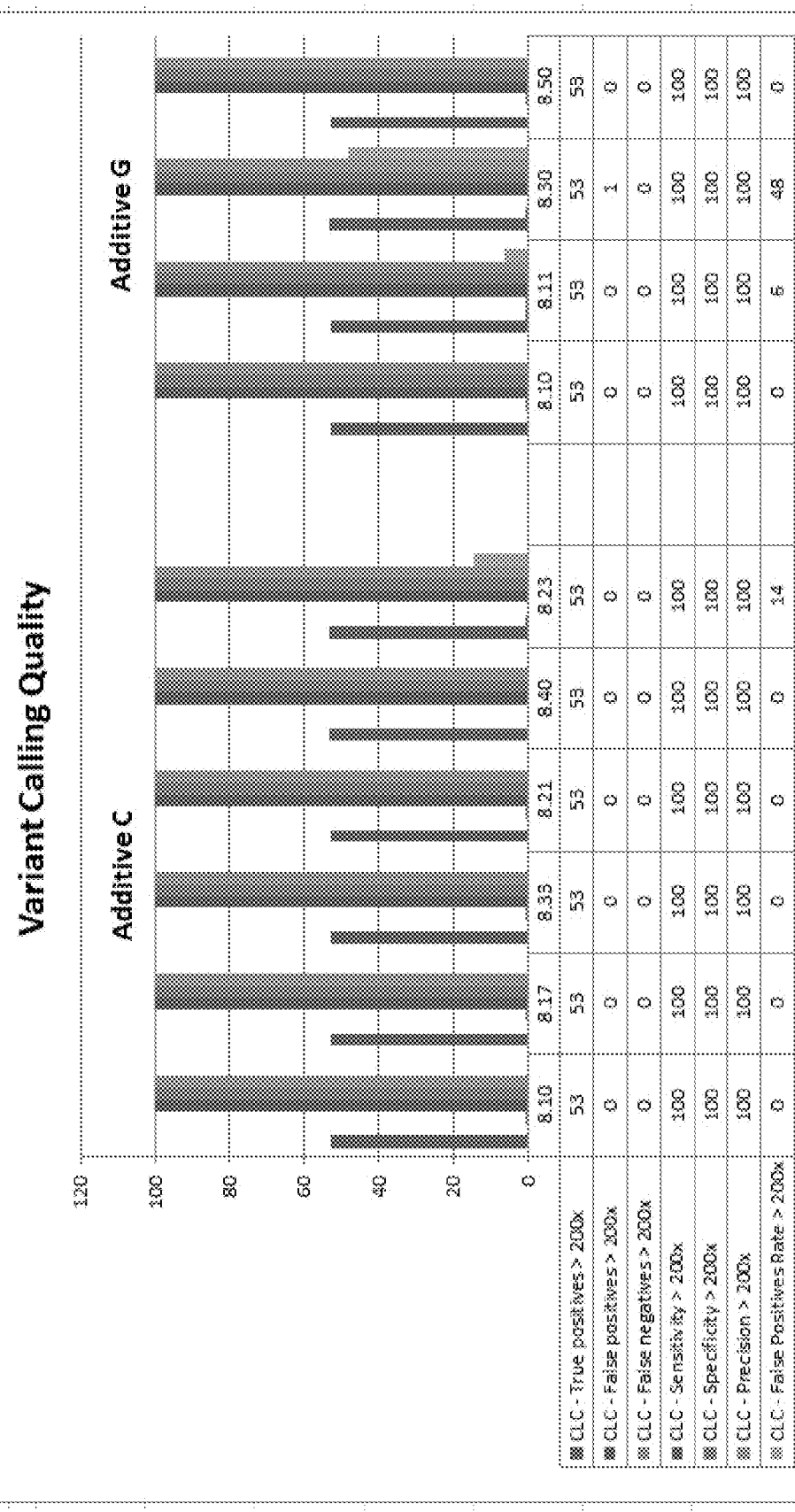
FIG. 8 presents exemplary data showing hotspot variant calling quality comparable between IPA and gallic acid results.
Figure 10:
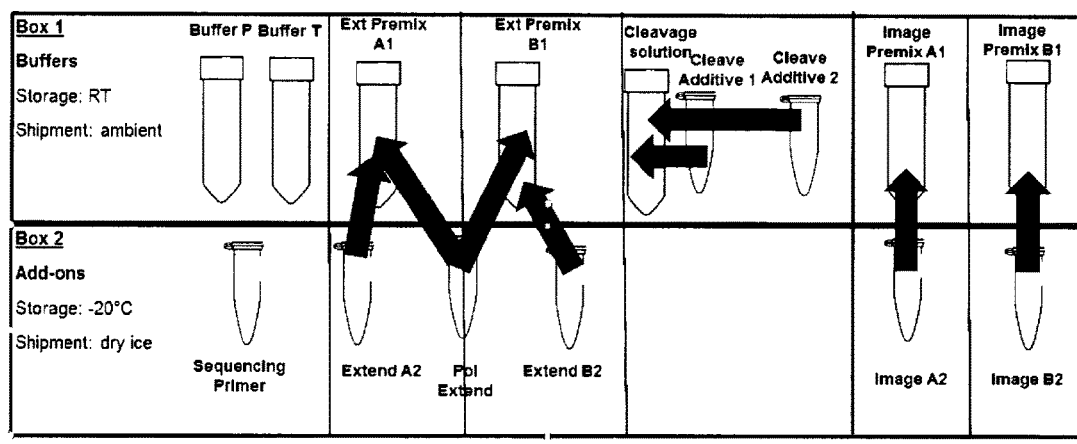
FIG. 10 describes one embodiment of the present invention comprising reagents are contained in each of the Sequencing Q Buffers (Box 1) and Sequencing Q Add-Ons (Box 2) packages, and how they are combined for 1 flow cell. The cleave reagent components are contained in Box 1 and in the new kit configuration have been re-labeled as follows: (a) Cleave Solution (Legacy buffer); (b) Cleave Additive 1 (New: IPA); and (c) Cleave Additive 2 (Legacy: TCEP). In using the kit, Extend A2 is to be added to the Ext Premix A1 and Pol Extend. Extend B2 is to be added to the Ext Premix B1 and Pol Extend. Additionally, the Cleave Additive 1 and Cleave Additive 2 should be added to the Cleavage solution. Additionally, Image A2 needs to be added to Image Premix A1 for use and Image B2 needs to be added to Image Premix B1 for use.

Subsequently, IPA was evaluated in a pre-system verification testing paradigm to generate a larger volume of sequencing statistics to determine both performance KPI's and instrument reliability KPI's. See, FIG. 1A-1B and FIG. 2. IPA was found to meet system KPI's over a large volume of statistics. In particular, an error rate of <0.5% and a filtered trimmed output of >1 Gb was determined. See, FIG. 3A-3B. Additionally, hotspot variant calling specifications were 100% for parameters including, but not limited to, specificity, sensitivity and precision. See, FIG. 8. Furthermore, no bead loss was observed for IPA and the comparative statistics for IPA and reference cleave agent, for example: i) IPA: 0% bead loss rate across 90 flow cells tested; and ii) gallic acid (GA): 30% bead loss rate across 30 flow cells tested. See, FIG. 4. This observation has been confirmed in other runs (data not shown) where it was determined that a baseline bead loss when using gallic acid occurs in approximately eleven (11) of thirty-one (31) flow cells (35%). In comparison, runs using IPA finds a complete absence of bead loss in zero (0) out of forty-four (44) flow cells (0%) and zero (0) out of fifty (50) flow cells. Even when using IPA guardbanding a low bead loss rate of one (1) of sixteen (16) flow cells was observed (6%).

Figure 5:
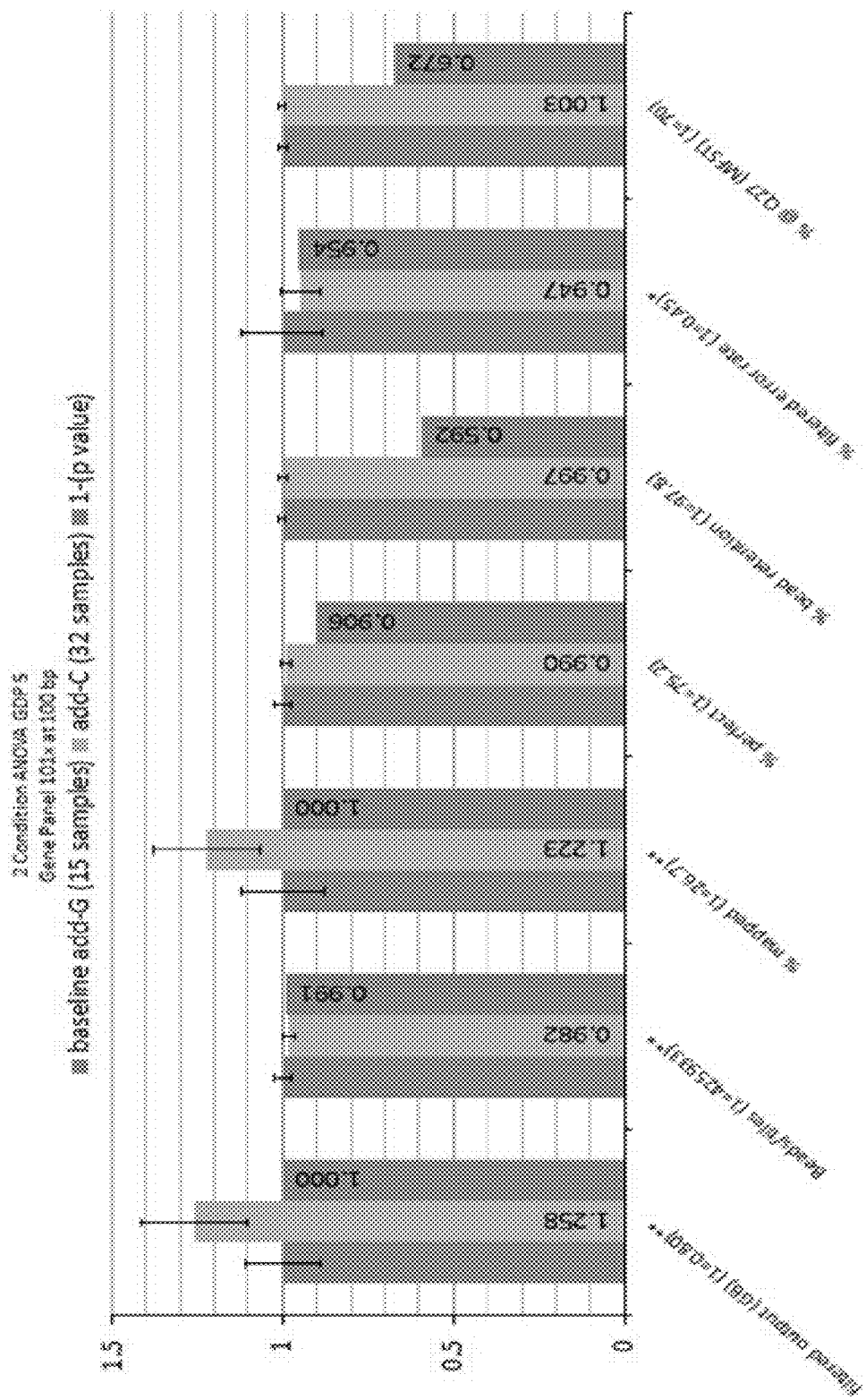
FIG. 5 presents exemplary data showing performance and reliability data between the comparative analysis between IPA and gallic acid.
Figure 6:
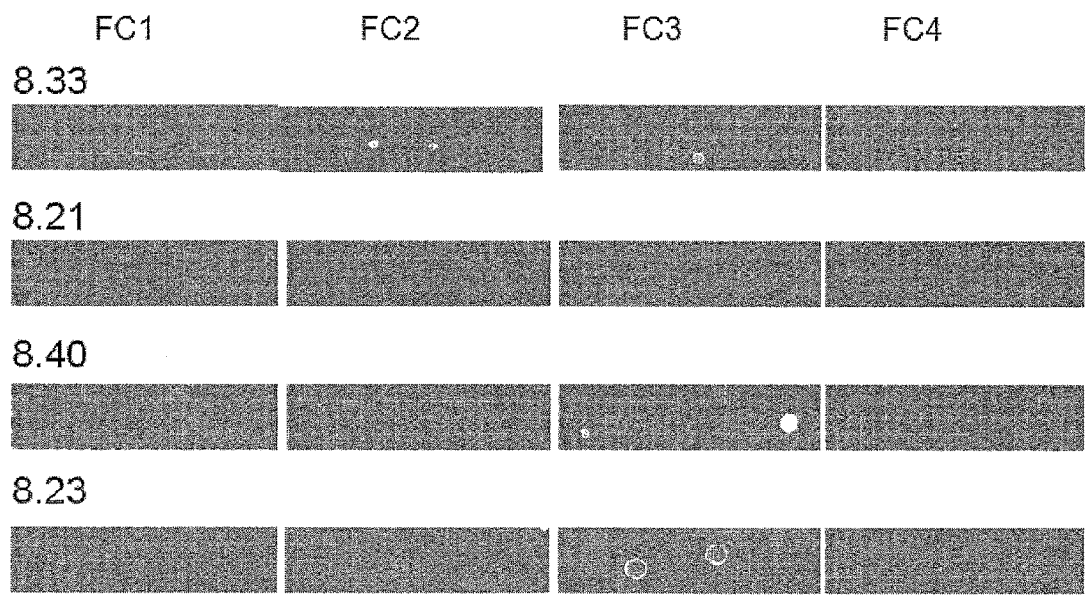
FIG. 6 presents exemplary data showing various read maps.
Figure 7:
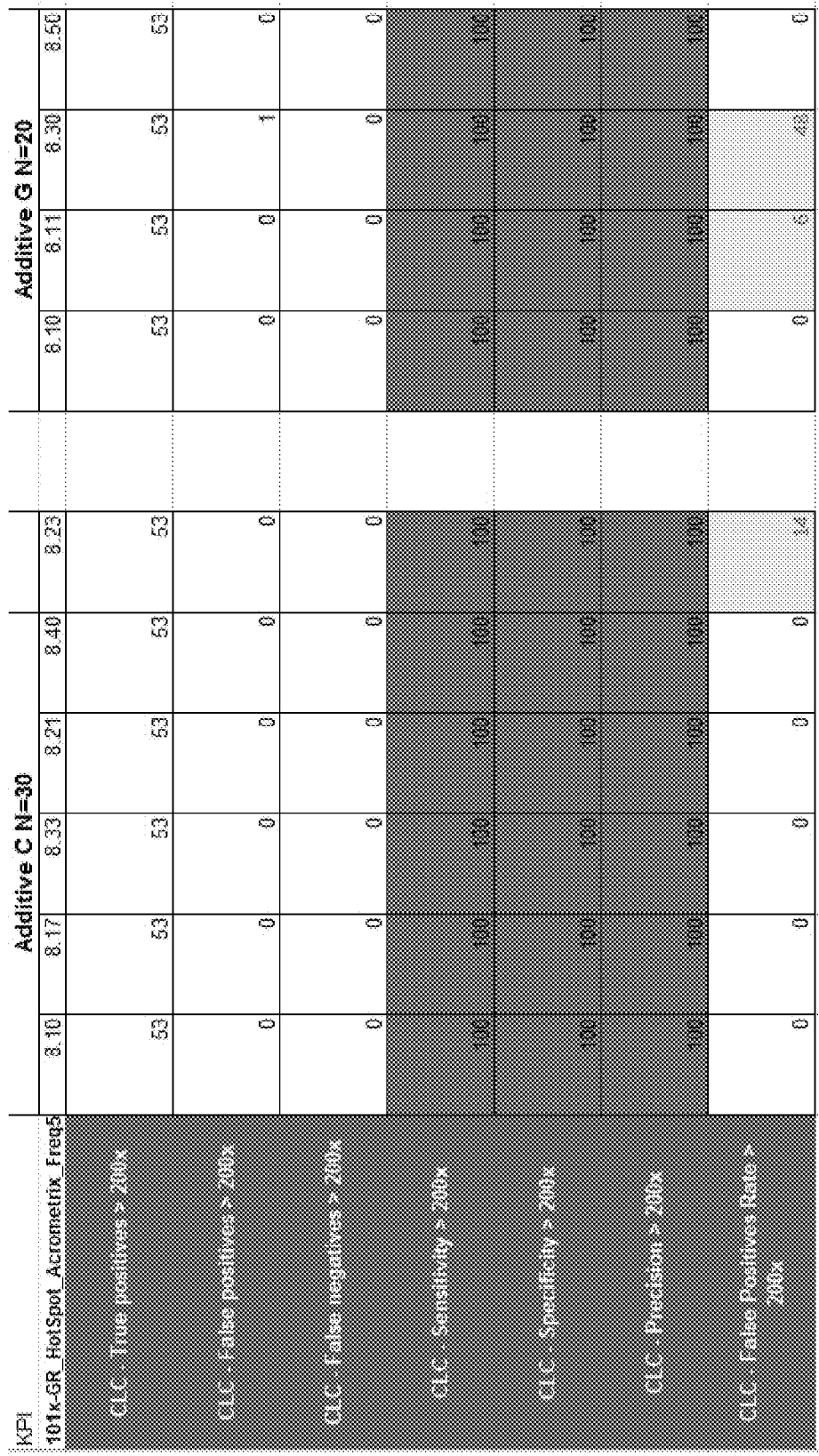
FIG. 7 presents exemplary data showing a base calling distribution from data comparing IPA and gallic acid.

The system performance and reliability was also evaluated. It was found that the performance of gallic acid and IPA was comparable and the higher throughput observed for gallic acid can be explained by the presence of more mapped reads. See, FIG. 5.

B. Carnitines

In some embodiments, the SBS method comprises a reactive oxygen species scavenger comprising a carnitine-based compound. In one embodiment, the carnitine-based compound is L-carnitine. In one embodiment, the carnitine-based compound is O-acetyl-carnitine. The data presented herein provides a preliminary early feasibility study to determine whether carnitine-based compounds can improve efficacy of a cleaving reagent during SBS. In particular, the structures of L-carnitine and O-acetyl-carnitine are shown below.

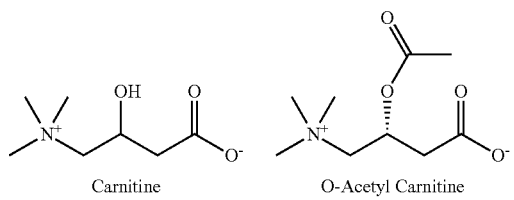

Carnitine and O-acetyl carnitine are similar to IPA with respect to radical scavenging behavior and anti-Alzheimer activity. Life Sci. 78:803 (2006); and Neurology 11:1726 (2006). In one embodiment, the present invention contemplates an SBS method comprising carnitine. In one embodiment, the present invention contemplates an SBS method comprising O-acetyl carnitine. In one embodiment, the present invention contemplates an SBS method comprising carnitine and O-acetyl carnitine. In one embodiment, the present invention contemplates an SBS method comprising carnitine and IPA. In one embodiment, the present invention contemplates an SBS method comprising O-acetyl carnitine and IPA. In one embodiment, the present invention contemplates an SBS method comprising carnitine, O-acetyl carnitine and IPA.

L-carnitine and O-acetyl-carnitine were tested for solubility and stability in cleave reagent formulations similarly to IPA. They were found to be highly soluble over a range of concentrations and stable against discoloration and precipitation upon storage at room temperature. See, Example V.

IV. An SBS Automated Instrument

In one embodiment, the present invention contemplates using an optical system, for exciting and measuring fluorescence on or in samples comprising fluorescent materials (e.g., fluorescent labels, dyes or pigments). In a further embodiment, a device is used to detect fluorescent labels on nucleic acid. In another embodiment, the device comprises a fluorescent detection system and a flow cell for processing biomolecules (e.g., nucleic acid samples) arrayed on a "chip" or other surface (e.g., microscope slide, etc.). The flow cell permits the user to perform biological reactions, including but not limited to, hybridization and sequencing of nucleic acids.

It is not intended that the present invention be limited to particular light sources. By way of example only, the system can employ ultra-bright LEDs (such as those available from Philips Lumileds Lighting Co., San Jose, Calif.) of different colors to excite dyes attached to the arrayed nucleic acids. These LEDs are more cost effective and have a longer life than conventionally used gas or solid state lasers. Other non-lasing sources of lights such as incandescent or fluorescent lamps may also be used.

It is not intended that the present invention be limited to particular light collection devices. By way of example only, the system may employ a high sensitivity CCD camera (such as those available from Roper Scientific, Inc., Photometric division, Tucson Ariz. or those available from Apogee Instruments, Roseville, Calif.) to image the fluorescent dyes and make measurements of their intensity. The CCD cameras may also be cooled to increase their sensitivity to low noise level signals. These may also be CMOS, vidicon or other types of electronic camera systems.

In one embodiment, the chip containing the array of nucleic acid spots is processed in a transparent flow cell incorporated within the instrument, which flows reagent past the spots and produces the signals required for sequencing. In a particular embodiment, the chip remains in the flow cell while it is imaged by the LED detector. The flow cell and associated reagents adds the nucleic acids, enzymes, buffers, etc. that are required to produce the fluorescent signals for each sequencing step, then the flow cell delivers the required reagents to remove the fluorescent signals in preparation for the next cycle. Measurement by the detector occurs between these two steps. In order for reactions to take place, the flow channels are configured to be of sufficient dimensions. For example, the flow-cell fluid channel formed by the array and the flat surface of the flow cell are at least 0.1 mm in depth (more particularly 0.5 mm in depth) and the volume formed by the chip, the block and the seal is at least 100 microliters in volume (more particularly, between 100 and 700 microliters, and still more particularly, between 150 and 300 microliters, e.g. 200 microliters, in volume).

In one embodiment, the flow cell is motionless (i.e., not moved during reactions or imaging). On the other hand, the flow cell can readily be mounted on a rotary or one or more linear stages, permitting movement. For example, in a two flow cell embodiment, the two flow cells may move up and down (or side to side) across the imaging system. Movement may be desired where additional processes are desired (e.g., where exposure to UV light is desired for photochemical reactions within the flow cell, such as removal of photocleavable fluorescent labels), when multiple flow cells share a single camera, or when the field of view of the detection system is smaller than the desired area to be measured on the flow cell. The detector system may also be moved instead of or in addition to the flow cell.

In a further embodiment, the flow cell is in fluid communication with a fluidics system. In one embodiment, each bottle is pressurized with a small positive gas pressure. Opening the appropriate valve allows reagent to flow from the source bottle through the flow cell to the appropriate collection vessel(s). In one embodiment, the nucleotides and polymerase solutions are recovered in a separate collection bottle for re-use in a subsequent cycle. In one embodiment, hazardous waste is recovered in a separate collection bottle. The bottle and valve configuration allow the wash fluid to flush the entire valve train for the system as well as the flow cell. In one embodiment, the process steps comprise: 1) flushing the system with wash reagent, 2) introducing nucleotides (e.g. flowing a nucleotide cocktail) and polymerase, 3) flushing the system with wash reagent, 4) introducing de-blocking reagent (enzyme or compounds capable of removing protective groups in order to permit nucleic acid extension by a polymerase), 5) imaging, 6) introducing label removing reagent (enzyme or compounds capable of removing fluorescent labels), and 7) flushing the system with wash reagent.

IV. Nucleotides

The invention's compositions and methods contemplate using nucleotide sequences that contain nucleotides. The term "nucleotide" refers to a constituent (or building block)

of nucleic acids (DNA and RNA) that contain a purine base, such as adenine (A) and guanine (G), or a pyrimidine base, such as cytosine (C), uracil (U), or thymine (T)), covalently linked to a sugar, such as D-ribose (in RNA) or D-2-deoxyribose (in DNA), with the addition of from one to three phosphate groups that are linked in series to each other and linked to the sugar. The term "nucleotide" includes native nucleotides and modified nucleotides.

"Native nucleotide" refers to a nucleotide occurring in nature, such as in the DNA and RNA of cells. In contrast, "modified nucleotide" refers to a nucleotide that has been modified by man, such as using chemical and/or molecular biological techniques compared to the native nucleotide. The terms also include nucleotide analogs attached to one or more probes to facilitate the determination of the incorporation of the corresponding nucleotide into the nucleotide sequence. In one embodiment, nucleotide analogues are synthesized by linking a unique label through a cleavable linker to the nucleotide base or an analogue of the nucleotide base, such as to the 5-position of the pyrimidines (T, C and U) and to the 7-position of the purines (deaza-G and deaza-A), to use a small cleavable chemical moiety to cap the 3'-OH group of the deoxyribose or ribose, and to incorporate the nucleotide analogues into the growing nucleotide sequence strand as terminators (e.g. reversible terminators). In one embodiment, detection of the label will yield the sequence identity of the nucleotide. Upon removing the label (by cleaving the linker) and the 3'-OH capping group, the polymerase reaction will proceed to incorporate the next nucleotide analogue and detect the next base. Exemplary fluorescent moieties re described in Ju et al., U.S. Pat. No. 6,664,079, hereby incorporated by reference.

Other nucleotide analogs that contain markers, particularly cleavable markers, are also contemplated, such as those configured using allyl groups, azido groups, and the like, and which are further described below. The nucleotide compositions of the invention are particularly useful in massively parallel DNA Sequencing By Synthesis (SBS) approaches utilizing fluorophores as markers.

EXPERIMENTAL

Example 1

Verification And Testing Cleave Reagent

Materials

| Component | Supplier | Item # |
|---|---|---|
| Cleave solution 1, unadjusted (Legacy buffer) | In-house (OPS-style) | n.a. |
| Cleave solution 2 (Legacy TCEP) | In-house (OPS-style) | n.a. |
| Add C (New component: IPA) | Sigma Aldrich | 57410 |

Notes:
1. When assembling this reagent, be sure to pipet accurately. To aliquot 1.74 mL of solution, use P1000 pipet. When aliquoting 49.5 mL, use 50 mL pipet and a P1000 to get accurate measurements.

Procedure for Preparing ~36 mL of 50 mM IPA in Cleave Solution for 2 or 3FC Run:
1. Add 328 mg of IPA to conical tune.
2. Add 33 mL of Cleave 1, unadjusted, to IPA. Invert several times to dissolve IPA. Add 1.74 mL of Cleave 2.
3. Mix the final solution by inverting the tube up and down at least ten times.
4. Required: Check pH and record in a Set up sheet.

Procedure for Preparing ~53 mL of 50 mM IPA in Cleave Solution for 4 FC Run:
1. Add 491 mg of IPA to conical tube.
2. Add 49.5 mL of Cleave 1 to IPA. Invert several times to dissolve IPA. Add 2.61 mL of Cleave 2.
3. Mix the final solution by inverting the tube up and down at least ten times.
4. Required: Check pH and record.

After the run: Record the pH of the cleave solution.

Example II

Optimized Cleave Reagent

The scheme (below) shows which reagents are contained in each of the Sequencing Q Buffers (Box 1) and Sequencing Q Add-Ons (Box 2) packages, and how they are combined for 1 flow cell.

Cleave reagent components are contained in Box 1 and in the new kit configuration have been re-labeled as follows:
(a) Cleave Solution (Legacy buffer)
(b) Cleave Additive 1 (New: IPA)
(c) Cleave Additive 2 (Legacy: TCEP)

See tables in following pages for preparation of new Cleave Reagent containing IPA.

TABLE 3

Reagent preparation for Sequencing Q Kit (1) for running 1 flow cell.

| Sequencing Q Buffers (Box 1) component | Fill volume | Number of tubes | Add-On to be added by user |
|---|---|---|---|
| Extend Premix A1 | 17.35 ml | 1 | 177 μl Extend A2 and 177 μl of Pol Extend from Box 2 |
| Extend Premix B1 | 17.35 ml | 1 | 177 μl Extend B2 and 177 μl of Pol Extend from Box 2 |
| Cleavage Solution | 16.5 ml | 1 | 164 mg/1 tube of Cleave Additive 1 and 870 μl/1 tube of Cleave Additive 2 from Box 1 |
| Image Premix A1 | 17.35 ml | 1 | 354 μl Image A2 from Box 2 |
| Image Premix B1 | 17.64 ml | 1 | 360 μl Image B2 from Box 2 |

Preparation of IPA Cleave Reagent for 1 Flow Cell:

Add 164 mg of Cleave Additive 1 to Cleavage Solution. Mix the contents in the tube by inverting the tube at least 10 times, until Cleave Additive 1 is completely dissolved. If any residual Cleave Additive 1 remains in its original tube, pipette 500 ul of the Cleavage Solution into Cleave Additive 1 tube, vortex to mix. Transfer all liquid back into Cleavage Solution tube. Then, Add 870 ul of Cleave Additive 2 to the combined Cleavage Solution. Mix the contents in the tube by inverting the tube at least 10 times.

TABLE 4

Reagent preparation for Sequencing Q Kit (4) for running 2 flow cells.

| Sequencing Q Buffers (Box 1) component | Fill volume | Number of tubes | Add-On to be added by user |
|---|---|---|---|
| Extend Premix A1 | 2 tubes of 17.35 ml | 2 | 2 tubes of Extend A2 (177 μl from each tube) and 1 tube of Pol Extend (total of 354 μl) from Box 2 |
| Extend Premix B1 | 2 tubes of 17.35 ml | 2 | 2 tubes of Extend B2 (177 μl from each tube) and 1 tube of Pol Extend (total of 354 μl) from Box 2 |
| Cleavage Solution | 2 tubes of 16.5 ml | 2 | 2 tubes of Cleave Additive 1 (164 mg in each tube); 2 tubes of Cleave Additive 2 (870 μl in each tube) from Box 1 |
| Image Premix A1 | 2 tubes of 17.35 ml | 2 | 2 tubes of Image A2 (354 μl in each tube) from Box 2 |
| Image Premix B1 | 2 tubes of 17.64 ml | 2 | 2 tubes of Image B2 (360 μl in each tube) from Box 2 |

Preparation of IPA Cleave Reagent for 2 Flow Cells:
  Add 164 mg of Cleave Additive 1 to each of the Cleave Solution tubes. After addition, mix the contents in the tube by inverting the tubes at least 10 times, until Cleave Additive 1 is completely dissolved. If any residual Cleave Additive 1 remains in its original tube, pipette 500 ul of the Cleavage Solution into each of the Cleave Additive 1 tubes, vortex to mix. Transfer liquid back into corresponding Cleavage Solution tubes. Then, add 870 ul of Cleave Additive 2 to each of the two single Cleavage Solution tubes. After addition, mix the contents in the tube by inverting the tubes at least 10 times and finally pool in to one single tube.

TABLE 5

Reagent preparation for Sequencing Q Kit (4) for running 3 or 4 flow cells.

| Sequencing Q Buffers (Box 1) component | Fill volume | Number of tubes | Add-On to be added by user |
|---|---|---|---|
| Extend Premix A1 | 3 tubes of 17.35 ml | 3 | 3 tubes of Extend A2 (177 μl from each tube) and 1.5 tubes of Pol Extend (total of 531 μl) from Box 2 |
| Extend Premix B1 | 3 tubes of 17.35 ml | 3 | 3 tubes of Extend B2 (177 μl from each tube) and 1.5 tubes of Pol Extend (total of 531 μl) from Box 2 |
| Cleavage Solution | 3 tubes of 16.5 ml | 3 | 3 tube of Cleave Additive 1 (164 mg in each tube); 3 tubes of Cleave Additive 2 (870 μl from each tube) from Box 1 |
| Image Premix A1 | 3 tubes of 17.35 ml | 3 | 3 tubes of Image A2 (354 μl in each tube) from Box 2 |
| Image Premix B1 | 3 tubes of 17.64 ml | 3 | 3 tubes of Image B2 (360 μl in each tube) from Box 2 |

Preparation of IPA Cleave Reagent for 3-4 Flow Cells:
  Add 164 mg of Cleave Additive 1 to each of the three single Cleave Solution tubes. After addition, mix the contents in the tube by inverting the tubes at least 10 times, until Cleave Additive 1 is completely dissolved. If any residual Cleave Additive 1 remains in its original tube, pipette 500 ul of the Cleavage Solution into each of the Cleave Additive 1 tubes, vortex to mix. Transfer liquid back into corresponding Cleavage Solution tubes. Then, add 870 ul of Cleave Additive 2 to each of the three single Cleavage Solution tubes. After addition, mix the contents in the tube by inverting the tubes at least 10 times and finally pool in to one single tube.

Example III

GDP4 Testing: IPA Versus Gallic Acid

This example tests IPA and gallic acid in a head-to-head comparison to evaluate performance equivalency using back-to-back assays on four (4) reading instruments. A total of eight runs were performed where four (4) runs used IPA and four (4) runs used gallic acid. The IPA runs evaluated fifteen (15) flow cells and the gallic acid runs evaluated seven (7) flow cells. See, FIG. 1A. Average bead loading for all flow cells was about 430,000 beads/tile. See, FIG. 1B. All runs used the same gene panel pool: (OC1)-NA12878/101X/BC1-10 and the analysis chain utilized SI3 ADAM templates [fq→fastq→CLC]. See, FIG. 2.

In this initial study, IPA and gallic acid appear to be performance equivalent based on System KPI's and FP rate. One (1) out of seven (7) flow cells showed an approximate 30% bead loss for gallic acid whereas no flow cells showed any bead loss when using IPA. See, FIG. 4. This is consistent with the 10-15% failure rate that has been observed during preliminary gallic acid assays.

Testing on 8-series with new baseline configuration (88 tile and 101× panel) has been performed to verify initial observations from this feasibility study.

Example IV

IPA Solubility

This example tests alternative formulations and chemistry for a cleave mix including TCEP as a standard reducing agent and IPA as a radical oxygen scavenger. The goal is to test both solubility and the ease of implementation into a kit configuration.

Formation of solid components directly within a Cleave 1 solution using an IPA concentration curve (10 mM, 25 mM and 50 mM) was assessed by measuring solubility, color, precipitate observation and pH level.

The results of these observations are presented in Table 6.

TABLE 6

IPA Solubility Concentration Curve

| IPA Conc/ Temperature | Time Point (hours) | Solubility | Color | Precipitate | pH |
|---|---|---|---|---|---|
| 10 mM/RT | 0 | Excellent | Transparent No color | None | 12.88 |
| 10 mM/2-8 C.° | 0 | Excellent | Transparent No color | None | 12.81 |
| 25 mM RT | 0 | Excellent | Transparent Pale yellow | None | 12.78 |
| 25 mM/2-8 C.° | 0 | Excellent | Transparent Pale yellow | None | 12.75 |
| 50 mM/RT | 0 | Excellent | Transparent Pale yellow | None | 12.61 |
| 50 mM/2-8 C.° | 0 | Excellent | Transparent Pale yellow | None | 12.67 |
| 10 mM/RT | 8 | Excellent | Transparent No color | None | 12.83 |
| 10 mM/2-8 C.° | 8 | Excellent | Transparent No color | None | 12.80 |
| 25 mM/RT | 8 | Excellent | Transparent Pale yellow | None | 12.67 |

TABLE 6-continued

IPA Solubility Concentration Curve

| IPA Conc/ Temperature | Time Point (hours) | Solubility | Color | Precipitate | pH |
|---|---|---|---|---|---|
| 25 mM/2-8 C.° | 8 | Excellent | Transparent Pale yellow | None | 12.71 |
| 50 mM/RT | 8 | Excellent | Transparent Pale yellow | None | 12.69 |
| 50 mM/2-8 C.° | 8 | Excellent | Transparent Pale yellow | None | 12.61 |
| 10 mM/RT | 48 | Excellent | Transparent No color | None | 12.79 |
| 10 mM/2-8 C.° | 48 | Excellent | Transparent No color | None | 12.83 |
| 25 mM/RT | 48 | Excellent | Transparent Pale yellow | None | 12.71 |
| 25 mM/2-8 C.° | 48 | Excellent | Transparent Pale yellow | None | 12.76 |
| 50 mM/RT | 48 | Excellent | Transparent Pale yellow | None | 12.72 |
| 50 mM/2-8 C.° | 48 | Excellent | Transparent Pale yellow | None | 12.64 |

These results show that IPA is highly soluble in aqueous solution at a pH ~12 and demonstrates relative stability as shown by lack of discoloration and/or formation of precipitate.

Example V

Carnitine Solubility

This example tests carnitine-based compounds for solubility into Cleave reagent. Various concentrations (10 mM, 25 mM and 50 mM) of carnitine and acetylcarnitine were tested for solubility and stability. The data (not shown) demonstrates that both compounds are very soluble across the tested range of concentrations. The solutions also appeared stable at room temperature (RT) in that no discoloration or precipitate were observed after a few hours of storage.

I claim:

1. A method of incorporating labeled nucleotides, comprising:
   a) providing i) a plurality of nucleic acid primers and template molecules, ii) a polymerase, iii) a cleave reagent comprising a scavenger selected from the group consisting of indole-3-propionic acid and a carnitine-based compound, and iv) a plurality of nucleotide analogues wherein at least a portion of said nucleotide analogues is labeled with a label attached through a cleavable disulfide linker to the base;
   b) hybridizing at least a portion of said primers to at least a portion of said template molecules so as to create hybridized primers;
   c) incorporating a first labeled nucleotide analogue with said polymerase into at least a portion of said hybridized primers so as to create extended primers comprising an incorporated nucleotide analogue; and
   d) cleaving the cleavable linker of said incorporated nucleotide analogues with said cleave reagent.

2. The method of claim 1, wherein said scavenger is indole-3-propionic acid.

3. The method of claim 1, wherein said scavenger is L-carnitine.

4. The method of claim 1, wherein said scavenger is O-acetyl-L-carnitine.

5. The method of claim 1, wherein said incorporated nucleotide analogues of step c) further comprise a removable chemical moiety capping the 3'-OH group.

6. The method of claim 5, wherein the cleaving of step d) removes the removable chemical moiety capping the 3'-OH group.

7. The method of claim 6, wherein the method further comprises:
   d) incorporating a second nucleotide analogue with said polymerase into at least a portion of said extended primers.

8. The method of claim 7, wherein said incorporating of a second nucleotide analogue is performed in the presence of a scavenger selected from the group consisting of indole-3-propionic acid and a carnitine-based compound.

9. A method of incorporating nucleotides, comprising:
   a) providing i) a plurality of nucleic acid primers and template molecules, and ii) an extend reagent, said extend reagent comprising polymerase, a plurality of nucleotide analogues, and a scavenger selected from the group consisting of indole-3-propionic acid and a carnitine-based compound;
   b) hybridizing at least a portion of said primers to at least a portion of said template molecules so as to create hybridized primers; and
   c) exposing said hybridized primers to said extend reagent under conditions such that a first nucleotide analogue is incorporated into at least a portion of said hybridized primers so as to create extended primers comprising an incorporated nucleotide analogue.

10. The method of claim 9, wherein said incorporated nucleotide analogue comprises a label attached through a cleavable disulfide linker to the base.

11. The method of claim 10, wherein said label is fluorescent.

12. The method of claim 9, wherein said extend reagent further comprises cystamine.

13. The method of claim 10, further comprising:
   d) cleaving the cleavable linker of said incorporated nucleotide analogue with a cleave reagent comprising a scavenger selected from the group consisting of indole-3-propionic acid and a carnitine-based compound.

14. The method of claim 9, wherein said scavenger is indole-3-propionic acid.

15. The method of claim 9, wherein said scavenger is L-carnitine.

16. The method of claim 9, wherein said scavenger is O-acetyl-L-carnitine.

17. The method of claim 13, wherein said incorporated nucleotide analogues prior to step d) further comprise a removable chemical moiety capping the 3'-OH group.

18. The method of claim 17, wherein the cleaving of step d) removes the removable chemical moiety capping the 3'-OH group.

19. A method of incorporating nucleotides, comprising:
   a) providing i) a plurality of nucleic acid primers and template molecules, ii) an extend reagent comprising polymerase and a plurality of nucleotide analogues, and iii) a wash reagent comprising a scavenger selected from the group consisting of indole-3-propionic acid and a carnitine-based compound;
   b) hybridizing at least a portion of said primers to at least a portion of said template molecules so as to create hybridized primers;
   c) exposing said hybridized primers to said extend reagent under conditions such that a first nucleotide analogue is incorporated into at least a portion of said hybridized primers so as to create extended primers comprising an incorporated nucleotide analogue;

d) washing said extended primers with said wash reagent.

20. The method of claim 19, wherein said incorporated nucleotide analogue comprises a label attached through a cleavable disulfide linker to the base.

21. The method of claim 20, wherein said label is fluorescent.

22. The method of claim 20, wherein said extend reagent further comprises cystamine.

23. The method of claim 20, further comprising:
e) detecting said label of a first labeled nucleotide analogue.

24. The method of claim 23, wherein said detecting of step e) is performed in the presence of a scavenger selected from the group consisting of indole-3-propionic acid and a carnitine-based compound.

25. The method of claim 19, wherein said scavenger is indole-3-propionic acid.

26. The method of claim 19, wherein said scavenger is L-carnitine.

27. The method of claim 19, wherein said scavenger is O-acetyl-L-carnitine.

28. A method of incorporating labeled nucleotides, comprising:
a) providing i) a plurality of nucleic acid primers and template molecules, ii) an extend reagent comprising polymerase and a plurality of nucleotide analogues wherein at least a portion of said nucleotide analogues is labeled, and iii) an image reagent comprising a scavenger selected from the group consisting of indole-3-propionic acid and a carnitine-based compound;
b) hybridizing at least a portion of said primers to at least a portion of said template molecules so as to create hybridized primers;
c) exposing said hybridized primers to said extend reagent under conditions such that a first labeled nucleotide analogue is incorporated into at least a portion of said hybridized primers so as to create extended primers comprising an incorporated nucleotide analogue; and
d) detecting said label of said first labeled nucleotide analogue with said image reagent.

29. The method of claim 28, wherein said label is attached through a cleavable disulfide linker to the base.

30. The method of claim 29, wherein said label is fluorescent.

31. The method of claim 28, wherein said extend reagent further comprises cystamine.

32. The method of claim 29, further comprising:
e) cleaving the cleavable linker of said incorporated nucleotide analogue with a cleave reagent comprising a scavenger selected from the group consisting of indole-3-propionic acid and a carnitine-based compound.

33. The method of claim 28, wherein said scavenger is indole-3-propionic acid.

34. The method of claim 28, wherein said scavenger is L-carnitine.

35. The method of claim 28, wherein said scavenger is O-acetyl-L-carnitine.

36. The method of claim 32, wherein said incorporated labeled nucleotide analogue of step d) further comprises a removable chemical moiety capping the 3'-OH group.

37. The method of claim 36, wherein the cleaving of step e) removes the removable chemical moiety capping the 3'-OH group.

* * * * *